US005773626A

United States Patent [19]
Kagano et al.

[11] Patent Number: 5,773,626
[45] Date of Patent: Jun. 30, 1998

[54] METHOD FOR PRODUCING 1,2-BENZISOTHIAZOL-3-ONES

[75] Inventors: Hirokazu Kagano; Hiroshi Goda; Katsuhiko Yoshida; Mikio Yamamoto; Shigeki Sakaue, all of Hyogo-ken, Japan

[73] Assignee: Sumitomo Seika Chemicals Co., Ltd., Hyogo-ken, Japan

[21] Appl. No.: 718,132

[22] Filed: Sep. 18, 1996

Related U.S. Application Data

[62] Division of Ser. No. 467,829, Jun. 6, 1995, Pat. No. 5,633,384.

[30] Foreign Application Priority Data

| Jul. 5, 1994 | [JP] | Japan | 6-177499 |
| Jul. 18, 1994 | [JP] | Japan | 6-188883 |
| Nov. 9, 1994 | [JP] | Japan | 6-301348 |

[51] Int. Cl.$^6$ .................................................. C07D 275/04
[52] U.S. Cl. .................................................................. 548/209
[58] Field of Search ............................................... 548/209

[56] References Cited

FOREIGN PATENT DOCUMENTS

| 2503699 | 8/1976 | European Pat. Off. . |
| 0314450 | 5/1989 | European Pat. Off. . |
| 0419075 | 3/1991 | European Pat. Off. . |
| 0530136 | 3/1993 | European Pat. Off. . |
| 7196638 | 8/1995 | Japan . |
| WO9523133 | 8/1995 | WIPO . |
| WO9523134 | 8/1995 | WIPO . |

OTHER PUBLICATIONS

A. Ricci, A. Martini 'Nuove sintesi del benzoisotiazolo', Ann. Chemica, vol. 53, No. 5, 1963, pp. 577–587.
A.J. Lawson, 'Thermal fission of hydroxylamine derivatives with neighbouring–group participation by thioether functions: preparation of 1,2–benzoisothiazoles', vol. 12, 1982 pp. 357–367.
F. Becke, H. Hagen 'Eine neue Synthese von 1.2–Benzoisothiazolen', Ann. Chem., vol. 729, 1969, pp. 146–151.
D. Hellwinkel, R. Karle 'Ein bequemes Eintopfverfahren zur Synthese von 1,2–Benziosothiazol–1,1–dioxiden', Synthesis, No. 5, 1989, pp. 394–395.

M.L. Carmellino et al 'Antimicrobial activity of fluorinated 1,2–benzisothiazol–3(2H)–ones and 2,2'–dithiobis(benzamides)', Eur.J.Med.Chem.Chim.Ther., vol. 29, No. 10, 1994, pp. 743–752.

Y. Uchida, S. Kozuka 'The Thermal Decomposition of N,O–Diacyl–N–t–butylhydroxylamines. III. Novel Routes to 2–Substituted 1,2–Benzoisothiazol–3–(2H)–ones', Bull. Chem. Soc. Jpn., vol. 55, No. 4, 1982, pp. 1183–1187.

"An Improved Mehtod for the Preparation of 2–Substituted 1,2–Benzisothiazol–3(2H)–Ones. Novel Cyclization of N–Substituted 2–Carbamoylbenzenesulfenyl Bromides on Activated Basic Alumina," Kamigata et al., Organic Preparations and Procedures Int., 15(5), 315–319 (1983).

"The Thermal Decomposition of N,O–Diacyl–N–t–butylhydroxylamines. III Novel Routes to 2–Substituted 1,2–Benzisothiazol–3–(2H)–ones," Uchida et al., Bull. Chem. Soc. Jpn., 55, 1183–1187 (1982).

McKinnon et al., (1987), Canadian J. Chem. vol. 66, pp. 1405–1409.

Journal of Organic Chemistry, (1978), vol. 43, No. 8, pp. 1604–1606.

Clifford et al., (1988), Pestic. Sci. 24, 111–121.

Markert et al., (1980), Liebigs Ann. Chem. 1990, pp. 768–778.

Derwent World Patent Index 94–290881 (1994).

Derwent World Patent Index 92–002646 (1992).

*Primary Examiner*—Patricia L. Morris
*Attorney, Agent, or Firm*—Birch, Stewart, Kolasch & Birch, LLP

[57] ABSTRACT

A method for producing a 1,2-benzisothiazol-3-one, having the steps of carrying out a reaction of a 2-(alkylthio) benzaldehyde with a hydroxylamine to give a 2-(alkylthio) benzaldehyde oxime and carrying out a reaction of the 2-(alkylthio)benzaldehyde oxime with a halogenating agent; and a method for producing a 1,2-benzisothiazol-3-one, having the steps of carrying out a reaction of a 2-halobenzonitrile with an alkanethiol in a heterogeneous solvent system in the presence of a base to give a 2-(alkylthio)benzonitrile and carrying out a reaction of the 2-(alkylthio)benzonitrile with an halogenating agent in the presence of water.

4 Claims, No Drawings

METHOD FOR PRODUCING 1,2-BENZISOTHIAZOL-3-ONES

This application is a divisional of application Ser. No. 08/467,829, filed on Jun. 6, 1995, now U.S. Pat. No. 5,633,384, the entire contents of which are hereby incorporated by reference.

BACKGROUND OF THE INVENTION

1. Field of the Invention

The present invention relates to a novel method for producing 1,2-benzisothiazol-3-ones, using 2-(alkylthio) benzaldehydes or 2-(alkylthio)benzaldehyde oximes as starting materials. The present invention also relates to a novel method for producing 2-(alkylthio)benzonitriles using 2-halobenzonitriles as starting materials, and to a novel method for producing 1,2-benzisothiazol-3-ones from the 2-(alkylthio)benzonitriles obtained by the method of the present invention. 1,2-benzisothiazol-3-ones are compounds useful as antibacterial agents and antifungal agents.

2. Discussion of the Related Art

The following methods are known for producing 1,2-benzisothiazol-3-ones.

(A) Bull. Chem. Soc. Jpn., 55, 1183–1187 (1982)

In this method, 2-(methylthio)benzamide is produced from 2-(methylthio)benzoyl chloride; oxidized with periodic acid to 2-(methylsulfinyl)benzamide; and cyclized in the presence of thionyl chloride to yield a 1,2-benzisothiazol-3-one.

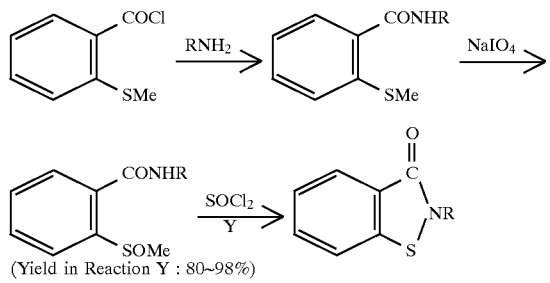

(Yield in Reaction Y : 80~98%)

(B) Org. Prep. Proced. Int., 15, 315–319(1983)

In this method, a 1,2-benzisothiazol-3-one is obtained in 4 steps, using thiosalicylic acid as a starting material.

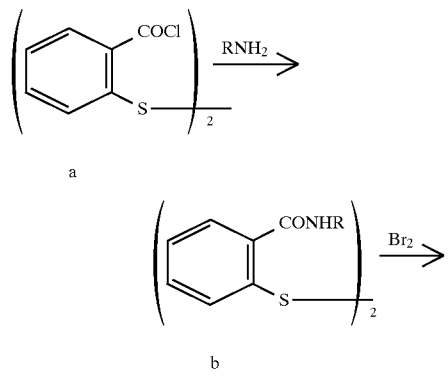

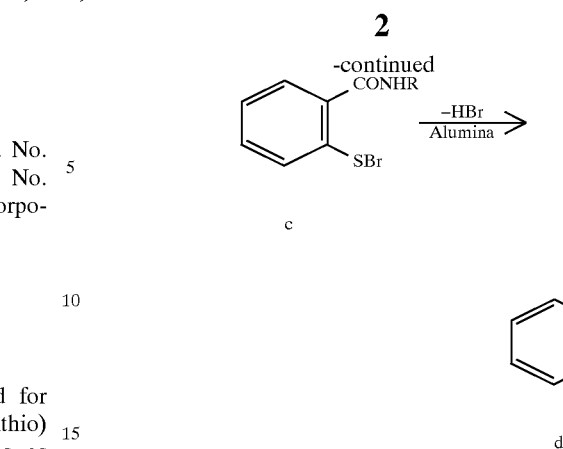

(Yield of d against b : 84~96%)

(C) Ger. Offen. 3500577 (1986)

In this method, a desired 1,2-benzisothiazol-3-one is obtained using thiosalicylic acid as a starting material and sodium hydroxide in the final cyclization process.

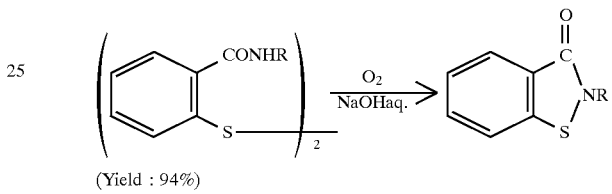

(Yield : 94%)

The present applicant have filed patent applications for the following methods as modified methods of the above known methods.

(D) Japanese Patent Application No. 5-350932 titled "A method for producing 1,2-benzisothiazol-3-ones" filed on Dec. 29, 1993.

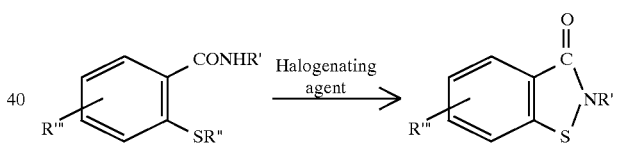

(E) Japanese Patent Application No. 6-151476 titled "A method for producing isothiazolone derivatives" filed on Jun. 8, 1994.

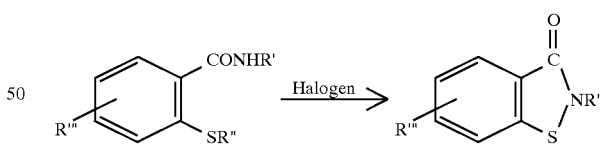

However, the above known conventional methods have the following drawbacks:

In Method (A), the starting 2-(methylthio)benzoyl chloride has problems of high production cost and poor stability. This method also requires the use of an expensive periodic acid which is dangerous in handling and involves many reaction steps.

Methods (B) and (C) require the use of expensive thiosalicylic acid as the starting material and involve many reaction steps. Therefore, this method is not satisfactory for industrial use.

Methods (D) and (E) proposed by the present applicant are modifications of the above conventional methods, where a starting 2-(alkylthio)benzamide reacts with a halogenating agent.

3

As stated above, all known methods are not satisfactory for production on an industrial scale.

SUMMARY OF THE INVENTION

Accordingly, an object of the present invention is to provide a simple and economical method for producing 1,2-benzisothiazol-3-ones on an industrial scale, without using materials which are costly and dangerous in handling.

Another object of the present invention is to provide a novel method for producing 2-(alkylthio)benzonitriles which are intermediates for the production of 1,2-benzisothiazol-3-ones.

In order to achieve the above objects, the present inventors made intensive studies to provide an easy and economically advantageous method for producing 1,2-benzisothiazol-3-ones without using materials which are costly and dangerous in handling. As a result, the inventors found that a 1,2-benzisothiazol-3-one represented by the general formula (III) can be obtained by treating a 2-(alkylthio)benzaldehyde oxime represented by the general formula (II) with a halogenating agent, the 2-(alkylthio) benzaldehyde oxime being obtained by the reaction of a 2-(alkylthio)benzaldehyde represented by the general formula (I) with a hydroxylamine.

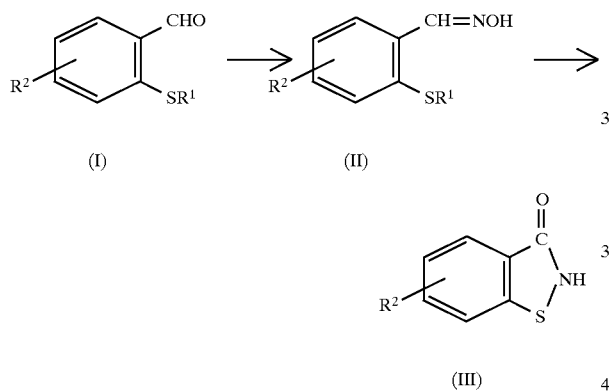

wherein $R^1$ represents an alkyl group having 1 to 4 carbon atoms, and $R^2$ represents a hydrogen atom, an alkyl group having 1 to 4 carbon atoms, an alkoxy group having 1 to 4 carbon atoms, a nitro group, a carboxyl group or an ester thereof, or a halogen atom.

Specifically, the present inventors noted that a 2-(alkylthio)benzaldehyde oxime represented by the general formula (II) is easily obtained by the reaction of a 2-(alkylthio)benzaldehyde represented by the general formula (I) with a hydroxylamine, and have found that a 1,2-benzisothiazol-3-one represented by the general formula (III) is obtained by further treating with a halogenating agent the 2-(alkylthio)benzaldehyde oxime represented by the general formula (II) obtained by the above reaction. The present inventors have also found that the series of the above reactions can be carried out as a one-pot process when a water-insoluble organic solvent system is used.

Also, the present inventors found that a 1,2-benzisothiazol-3-one represented by the general formula (III) can be obtained in one step by treating a 2-(alkylthio) benzonitrile represented by the general formula (IV) with a halogenating agent in the presence of water as shown below, the 2-(alkylthio)benzonitrile being obtained by the reaction of a 2-halobenzonitrile represented by the general formula (V) with an alkanethiol represented by the general formula (VI) in the presence of a base in a heterogeneous solvent system.

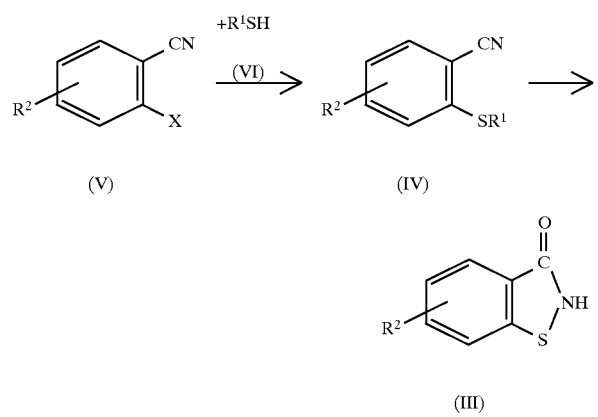

wherein $R^1$ represents an alkyl group having 1 to 4 carbon atoms, and $R^2$ represents a hydrogen atom, an alkyl group having 1 to 4 carbon atoms, an alkoxy group having 1 to 4 carbon atoms, a nitro group, a carboxyl group or an ester thereof, or a halogen atom.

Specifically, the present inventors discovered that a 2-(alkylthio)benzonitrile represented by the general formula (IV) is easily obtained by the reaction of a 2-halobenzonitrile represented by the general formula (V) with an alkanethiol represented by the general formula (VI) in the presence of a base in a heterogeneous solvent system.

The present inventors also found that a 1,2-benzisothiazol-3-one represented by the general formula (III) is obtained by further treating the 2-(alkylthio) benzonitrile obtained in the above reaction and represented by the general formula (IV) with a halogenating agent in the presence of water, and that when a water-insoluble organic solvent system is used as a solvent of the above reaction, a series of the above reactions to yield a 1,2-benzisothiazol-3-one from a 2-halobenzonitrile can be carried out in a one-pot process.

Based upon the above findings, the present inventors made further studies and have completed the present invention.

In brief, the present invention is concerned with:

(1) A method for producing a 1,2-benzisothiazol-3-one represented by the general formula (III), comprising carrying out a reaction of a 2-(alkylthio)benzaldehyde represented by the following general formula (I):

wherein $R^1$ represents an alkyl group having 1 to 4 carbon atoms, and $R^2$ represents a hydrogen atom, an alkyl group having 1 to 4 carbon atoms, an alkoxy group having 1 to 4 carbon atoms, a nitro group, a carboxyl group or an ester thereof, or a halogen atom, with a hydroxylamine to give a 2-(alkylthio)benzaldehyde oxime represented by the following general formula (II):

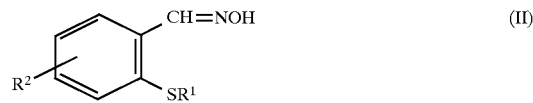

wherein $R^1$ and $R^2$ are defined as above; and carrying out a reaction of said 2-(alkylthio)benzaldehyde oxime with a halogenating agent to give a 1,2-benzisothiazol-3-one represented by the following general formula (III):

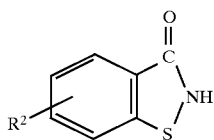

wherein $R^2$ is defined as above;

(2) A method for producing a 1,2-benzisothiazol-3-one represented by the general formula (III), comprising carrying out a reaction of a 2-(alkylthio)benzaldehyde oxime represented by the following general formula (II):

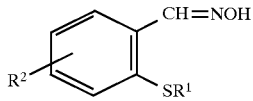

wherein $R^1$ represents an alkyl group having 1 to 4 carbon atoms, and $R^2$ represents a hydrogen atom, an alkyl group having 1 to 4 carbon atoms, an alkoxy group having 1 to 4 carbon atoms, a nitro group, a carboxyl group or an ester thereof, or a halogen atom, with a halogenating agent to give a 1,2-benzisothiazol-3-one represented by the following general formula (III):

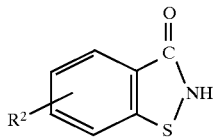

wherein $R^2$ is defined as above;

(3) A method for producing a 1,2-benzisothiazol-3-one represented by the general formula (III), comprising carrying out a reaction of a 2-(alkylthio)benzonitrile represented by the following general formula (IV):

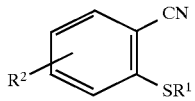

wherein $R^1$ represents an alkyl group having 1 to 4 carbon atoms, and $R^2$ represents a hydrogen atom, an alkyl group having 1 to 4 carbon atoms, an alkoxy group having 1 to 4 carbon atoms, a nitro group, a carboxyl group or an ester thereof, or a halogen atom, with a halogenating agent in the presence of water to give a 1,2-benzisothiazol-3-one represented by the following general formula (III):

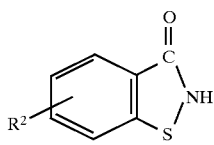

wherein $R^2$ is defined as above;

(4) A method for producing a 2-(alkylthio)benzonitrile represented by the general formula (IV), comprising carrying out a reaction of a 2-halobenzonitrile represented by the following general formula (V):

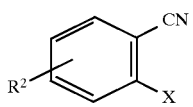

wherein X represents a chlorine atom or a bromine atom, and $R^2$ represents a hydrogen atom, an alkyl group having 1 to 4 carbon atoms, an alkoxy group having 1 to 4 carbon atoms, a nitro group, a carboxyl group or an ester thereof, or a halogen atom, with an alkanethiol represented by the following general formula (VI):

$$R^1SH \quad (VI)$$

wherein $R^1$ represents an alkyl group having 1 to 4 carbon atoms, in a heterogeneous solvent system in the presence of a base to give a 2-(alkylthio)benzonitrile represented by the following general formula (IV):

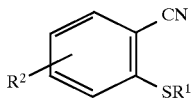

wherein $R^1$ and $R^2$ are defined as above; and (5) A method for producing a 1,2-benzisothiazol-3-one represented by the general formula (III), comprising carrying out a reaction of a 2-halobenzonitrile represented by the following general formula (V):

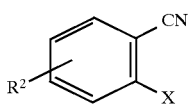

wherein X represents a chlorine atom or a bromine atom, and $R^2$ represents a hydrogen atom, an alkyl group having 1 to 4 carbon atoms, an alkoxy group having 1 to 4 carbon atoms, a nitro group, a carboxyl group or an ester thereof, or a halogen atom, with an alkanethiol represented by the following general formula (VI):

$$R^1SH \quad (VI)$$

wherein $R^1$ represents an alkyl group having 1 to 4 carbon atoms, in a heterogeneous solvent system in the presence of a base to give a 2-(alkylthio)benzonitrile represented by the following general formula (IV):

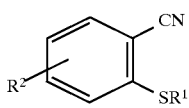

wherein $R^1$ and $R^2$ are defined as above; and carrying out a reaction of said 2-(alkylthio)benzonitrile with a halogenating agent in the presence of water to give a 1,2-benzisothiazol-3-one represented by the following general formula (III):

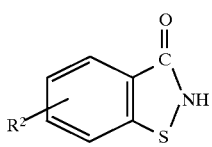

wherein $R^2$ is defined as above.

According to the process of the present invention, 1,2-benzisothiazol-3-ones, compounds useful as antibacterial or antifungal agents, can easily be produced in high yield in short process without using expensive starting materials.

DETAILED DESCRIPTION OF THE INVENTION

The present invention will be explained in detail below by explaining the following two embodiments of the present invention:

Embodiment I: A method for producing a 1,2-benzisothiazol-3-one by treating with a halogenating agent a 2-(alkylthio)benzaldehyde oxime represented by the general formula (II) that is obtained by the reaction between a 2-(alkylthio)benzaldehyde represented by the general formula (I) and a hydroxylamine; and Embodiment II: A method for producing a 1,2-benzisothiazol-3-one, wherein a 2-(alkylthio)benzonitrile represented by the general formula (IV) is treated with a halogenating agent in the presence of water in one step to yield a 1,2-benzisothiazol-3-one, the 2-(alkylthio) benzonitrile being obtained by the reaction of a 2-halobenzonitrile represented by the general formula (V) with an alkanethiol represented by the general formula (VI) in the presence of a base in a heterogeneous solvent system.

Embodiment I

The feature of Embodiment I of the present invention is in that a 1,2-benzisothiazol-3-one is produced by simple procedures where a 2-(alkylthio)benzaldehyde oxime that can readily be obtained from a 2-(alkylthio)benzaldehyde is cyclized by the action of a halogenating agent. Another feature of this embodiment lies in that a 1,2-benzisothiazol-3-one can efficiently and easily be produced in a one-pot process where a 2-(alkylthio)benzaldehyde is treated with a hydroxylamine to yield a 2-(alkylthio)benzaldehyde oxime in a water-insoluble organic solvent; the solvent layer containing the oxime is separated; and a halogenating agent is added to the solvent to yield a 1,2-benzisothiazol-3-one.

$R^1$ in the above general formulas (I) and (II) stands for an alkyl group having 1 to 4 carbon atoms. Alkyl groups represented by $R^1$ are exemplified by methyl, ethyl, n-propyl, isopropyl, n-butyl, isobutyl, sec-butyl and tert-butyl groups, with a preference given to methyl, ethyl, n-propyl, and tert-butyl groups.

$R^2$ in the general formulas (I), (II), and (III) stands for a hydrogen atom, an alkyl group having 1 to 4 carbon atoms, an alkoxy group having 1 to 4 carbon atoms, a nitro group, a carboxyl group or an ester thereof, or a halogen atom. Alkyl groups represented by $R^2$ are exemplified by methyl, ethyl, n-propyl, isopropyl, n-butyl, isobutyl, sec-butyl, and tert-butyl groups. Alkoxy groups represented by $R^1$ are exemplified by methoxy, ethoxy, propoxy, and butoxy groups. Esters of carboxyl group represented by $R^2$ are exemplified by methoxy carbonyl, ethoxy carbonyl, propoxy carbonyl, and butoxy carbonyl. Halogen atoms represented by $R^2$ are exemplified by a chlorine atom and a bromine atom. Preferred examples of $R^2$ include a hydrogen atom, a chlorine atom, and a nitro group.

In the present method, an oxime is first formed by treating an 2-(alkylthio)benzaldehyde represented by the general formula (I) with hydroxylamine to yield a 2-(alkylthio) benzaldehyde oxime represented by the general formula (II).

Examples of 2-(alkylthio)benzaldehyde represented by the general formula (I) include:
2-(methylthio)benzaldehyde,
2-(ethylthio)benzaldehyde,
2-(n-propylthio)benzaldehyde,
2-(tert-butylthio)benzaldehyde,
3-methyl-2-(methylthio)benzaldehyde,
5-butyl-2-(methylthio)benzaldehyde,
4-methoxy-2-(methylthio)benzaldehyde,
2-methylthio-3-nitrobenzaldehyde,
4-chloro-2-(methylthio)benzaldehyde,
4-carboxy-2-(methylthio)benzaldehyde, and
4-methoxycarbonyl-2-(methylthio)benzaldehyde.

Among the above examples, 2-(methylthio) benzaldehyde, 2-(ethylthio)benzaldehyde, 2-(n-propylthio) benzaldehyde, and 2-(tert-butylthio)benzaldehyde are preferably used because they are readily available and can give products with high antibacterial activity.

Practically, hydroxylamines used in the present invention are supplied as mineral acid salts such as sulfates. Therefore, upon the reaction with 2-(alkylthio)benzaldehyde, the salt of hydroxylamine is neutralized with a base to release a free hydroxylamine in the solvent system.

Mineral acid salts of hydroxylamines usable in the present invention include hydrochloric acid salts and sulfates, with a preference given to sulfates from the economical viewpoint.

The hydroxylamine mineral acid salt is used normally in an amount of 0.8 to 3.0 moles, preferably 1.0 to 2.0 moles, per mole of 2-(alkylthio)benzaldehyde. When the amount of the salt is less than 0.8 moles, the amount of unchanged 2-(alkylthio)benzaldehyde tends to increase. On the other hand, even when the amount of the salt exceeds 3.0 moles, any extra effects cannot be obtained.

Examples of the base used for neutralizing the hydroxylamine mineral acid salt used in oxime formation process include alkali metal hydroxides such as sodium hydroxide and potassium hydroxide; alkali metal carbonates such as sodium carbonate and potassium carbonate; and metal alcoholates such as sodium methylate and sodium ethylate. Of these, sodium carbonate is preferably used in view of yield and cost.

The above-mentioned base is used in an adequate amount to neutralize the hydroxylamine mineral acid salt. Specifically, the amount of the base is 0.8 to 1.5 equivalents of the acid component of the hydroxylamine mineral acid salt. When the amount of the base is less than 0.8 equivalents of the acid component of the salt, the amount of unchanged 2-(alkylthio)benzaldehyde increases. On the other hand, even when the amount of the base exceeds 1.5 equivalents, any extra effects cannot be obtained, and, therefore, it is economically disadvantageous.

The reaction solvents used for the oxime formation process are not particularly limited as long as they are inert to the reaction. Examples of water-insoluble solvents include hydrocarbons, such as n-hexane, n-heptane, cyclohexane, methylcyclohexane, benzene, toluene and xylene; and halogenated hydrocarbons, such as methylene chloride, 1,2-dichloroethane and chlorobenzene. Examples of water-soluble solvents include alcohols, such as methanol, and ethanol.

Of the above solvents, a water-insoluble solvent allows to carry out the oxime formation reaction and the subsequent reaction of the resulting oxime with a halogenating agent in a one-pot process, and to facilitate the production of 1,2-benzisothiazol-3-one.

The amount of the solvent is normally 1 to 30 times the weight of 2-(alkylthio)benzaldehyde.

The reaction temperature for the oxime formation is normally in the range of from −20° to 100° C., preferably 0° to 80° C. Reaction temperatures higher than 100° C. cause problems of side reactions. On the other hand, reaction rate lowers to an impractical level when the reaction temperature is less than −20° C. The reaction time varies with the reaction temperature and the type of reaction solvent, and it is normally in the range between 1 and 40 hours.

A 2-(alkylthio)benzaldehyde oxime can be isolated and purified from the reaction mixture by a conventional method, i.e., by direct crystallization or by extraction and subsequent recrystallization.

Also, the 2-(-alkylthio)benzaldehyde oxime dissolved in the reaction solvent obtained by the above-mentioned method can directly be used as a starting material for the cyclization to yield a 1,2-benzisothiazol-3-one without being isolated and purified.

Next, a 2-(alkylthio)benzaldehyde oxime represented by the general formula (II) obtained by the above process is treated with a halogenating agent to yield a 1,2-benzothiazol-3-one represented by the general formula (III). This process hereinafter is referred to as a cyclization process.

Examples of 2-(alkylthio)benzaldehyde oximes represented by the general formula (II) include:
2-(methylthio)benzaldehyde oxime,
2-(ethylthio)benzaldehyde oxime,
2-(n-propylthio)benzaldehyde oxime,
2-(tert-butylthio)benzaldehyde oxime,
3-methyl-2-(methylthio)benzaldehyde oxime,
5-butyl-2-(methylthio)benzaldehyde oxime,
4-methoxy-2-(methylthio)benzaldehyde oxime,
2-methylthio-3-nitrobenzaldehyde oxime,
4-chloro-2-(methylthio)benzaldehyde oxime,
4-carboxy-2-(methylthio)benzaldehyde oxime, and
4-methoxycarbonyl-2-(methylthio)benzaldehyde oxime.

Among the above examples, 2-(methylthio)benzaldehyde oxime, 2-(ethylthio)benzaldehyde oxime, 2-(n-propylthio)benzaldehyde oxime, and 2-(tert-butylthio)benzaldehyde oxime are preferably used because they are readily available and can give products with high antibacterial activity.

Examples of halogenating agents usable in the present invention include chlorine, bromine, sulfuryl chloride and sulfuryl bromide, with a preference given to chlorine, bromine, and sulfuryl chloride from the economical viewpoint.

The halogenating agent is used normally in an amount of 0.8 to 3.0 moles, preferably 1.0 to 2.0 moles, per mole of 2-(alkylthio)benzaldehyde oxime. When the amount of the halogenating agent is less than 0.8 moles, the amount of unchanged 2-(alkylthio)benzaldehyde oxime tends to increase. On the other hand, even when the amount of the halogenating agent exceeds 3.0 moles, the yield tends to decrease due to the side reaction.

The reaction solvents used in the cyclization process above are not particularly limited as long as they are inert to the reaction. However, when a 1,2-benzisothiazol-3-one is obtained in a one-pot process, it is preferable to use the same reaction solvent as used in the oxime formation reaction. Examples of the solvents include hydrocarbons, such as n-hexane, n-heptane, cyclohexane, methylcyclohexane, benzene, toluene and xylene; and halogenated hydrocarbons, such as methylene chloride, 1,2-dichloroethane and chlorobenzene, with a preference given to monochlorobenzene and toluene. The amount of the solvent is normally 1 to 30 times the weight of 2-(alkylthio)benzaldehyde oxime.

The reaction temperature for the cyclization is normally in the range of from −20° to 170° C., preferably 0° to 150° C. Reaction temperatures higher than 170° C. cause problems of side reactions. On the other hand, reaction rate lowers to an impractical level when the reaction temperature is less than −20° C. The reaction time varies with the reaction temperature and the type of reaction solvent, and it is normally in the range between 1 and 40 hours.

A desired 1,2-benzisothiazol-3-one can be isolated and purified from the reaction mixture by a conventional method such as direct crystallization, and extraction followed by recrystallization. Other methods may also be used with no limitation.

Embodiment II

Embodiment II of the present invention is characterized in that a 1,2-benzisothiazol-3-one can easily be produced by cyclizing a 2-(alkylthio)benzonitrile, readily being obtained from a 2-halobenzonitrile, with a halogenating agent in the presence of water. Embodiment II is also characterized by producing a 1,2-benzisothiazol-3-one in a one-pot process by the steps of carrying out a reaction between a 2-halobenzonitrile and an alkanethiol in the presence of a base in a heterogeneous solvent system containing a water-insoluble solvent to yield a 2-(alkylthio)benzonitrile, separating oil layer containing the 2-(alkylthio)benzonitrile from water layer, treating the 2-(alkylthio)benzonitrile in the oil layer with a halogenating agent in the presence of water to yield a 1,2-benzisothiazol-3-one.

$R^1$ in the above general formulas (IV) and (VI) stands for an alkyl group having 1 to 4 carbon atoms. Alkyl groups represented by $R^1$ are exemplified by methyl, ethyl, n-propyl, isopropyl, n-butyl, isobutyl, and sec-butyl, tert-butyl groups, with a preference given to methyl, ethyl, n-propyl, and tert-butyl groups.

$R^2$ in the general formulas (IV), (III), and (V) stands for a hydrogen atom, an alkyl group having 1 to 4 carbon atoms, an alkoxy group having 1 to 4 carbon atoms, a nitro group, a carboxyl group or an ester thereof, or a halogen atom. Alkyl groups represented by $R^2$ are exemplified by methyl, ethyl, n-propyl, isopropyl, n-butyl, isobutyl, sec-butyl and tert-butyl groups. Alkoxy groups represented by $R^2$ are exemplified by methoxy, ethoxy, propoxy, and butoxy groups. Esters of carboxyl group represented by $R^2$ are exemplified by methoxy carbonyl, ethoxy carbonyl, propoxy carbonyl, and butoxy carbonyl. Halogen atoms represented by $R^2$ are exemplified by a chlorine atom and a bromine atom. Preferred examples of $R^2$ include a hydrogen atom, a methyl group, an ethyl group, a tert-butyl group, a methoxy group, a methoxy carbonyl group, an ethoxy carbonyl group, a propoxy carbonyl group, a chlorine atom, and a nitro group.

Examples of 2-(alkylthio)benzonitrile represented by the general formula (IV) include:
2-(methylthio)benzonitrile,
2-(ethylthio)benzonitrile,
2-(n-propylthio)benzonitrile,
2-(tert-butylthio)benzonitrile,
3-methyl-2-(methylthio)benzonitrile,
5-butyl-2-(methylthio)benzonitrile,
4-methoxy-2-(methylthio)benzonitrile,
2-methylthio-3-nitrobenzonitrile,
4-chloro-2-(methylthio)benzonitrile,
4-carboxy-2-(methylthio)benzonitrile, and
4-methoxycarbonyl-2-(methylthio)benzonitrile.

Of the above examples, 2-(methylthio)benzonitrile, 2-(ethylthio)benzonitrile, 2-(n-propylthio)benzonitrile, and 2-(tert-butylthio)benzonitrile are preferably used because they are readily available and can give products with high antibacterial activity.

Although the method for producing 2-(alkylthio) benzonitriles represented by the general formula (IV) is not limited, it is advantageous to use the method of the present invention. Specifically, a 2-(alkylthio)benzonitrile represented by the general formula (IV) is produced by the reaction of a 2-halobenzonitrile represented by the general formula (V) with an alkanethiol represented by the general formula (VI) in the presence of a base in a heterogeneous solvent system. In the general formula (V), X stands for a chlorine atom or a bromine; and $R^2$ stands for the same substituents as $R^2$ in the general formula (IV). $R^1$ in the general formula (VI) stands for the same substituents as $R^1$ in the general formula (IV).

Examples of 2-halobenzonitriles represented by the general formula (V) include 2-chlorobenzonitrile, 2-bromobenzonitrile, 3-methyl-2-chlorobenzonitrile, 5-butyl-2-chlorobenzonitrile, 4-methoxy-2-chlorobenzonitrile, 2-chloro-3-nitrobenzonitrile, and 4-methoxycarbonyl-2-chlorobenzonitrile.

Alkanethiols represented by the general formula (VI) are exemplified by methanethiol, ethanethiol, 1-propanethiol, and 2-butanethiol. The alkanethiol is used normally in an amount of 0.8 to 3.0 moles, preferably 1.0 to 2.0 moles, per mole of 2-halobenzonitrile used. When the amount of alkanethiol used is less than 0.8 moles, unchanged 2-halobenzonitrile increases. Even though the amount of alkanethiol exceeds 3.0 moles, additional effects cannot be expected, and, therefore, it is economically disadvantageous.

Bases which can be used in the reaction of a 2-halobenzonitrile with an alkanethiol include alkali metal hydroxides, such as sodium hydroxide and potassium hydroxide; alkali metal carbonates, such as sodium carbonate and potassium carbonate; and metal alcoholates, such as sodium methylate and sodium ethylate. From the economic viewpoint, sodium hydroxide is preferably used.

The base is used normally in an amount of 0.8 to 3.5 moles, preferably 1.0 to 2.5 moles, per mole of 2-halobenzonitrile used. When the amount of a base used is less than 0.8 moles, unchanged 2-halobenzonitrile increases. Even when the amount of base used exceeds 3.5 moles, additional effects cannot be expected, and, therefore, it is economically disadvantageous.

The present method for producing an 2-(alkylthio) benzonitrile is characterized in that the reaction is carried out in a heterogeneous solvent system in the presence of a base. The reaction of a starting 2-halobenzonitrile with an alkanethiol is carried out in a two-phase solvent system, because a 2-halobenzonitrile is insoluble in water. In this case, a phase-transfer catalyst is preferably added to the solvent system to promote the reaction. Phase-transfer catalysts which can be used for this purpose include quaternary ammonium salts, such as benzyltriethylammonium bromide, benzyltrimethylammonium chloride, hexadecyltriethylammonium bromide, hexadecyltrimethylammonium chloride, dodecyltrimethylammonium chloride, octyltriethylammonium bromide, tetra-n-butylammonium bromide, tetra-n-butylammonium chloride, tetraethylammonium chloride and trioctylmethylammonium chloride; quaternary phosphonium salts, such as hexadecyltriethylphosphonium bromide, hexadecyltributylphosphonium chloride, tetra-n-butylphosphonium bromide, tetra-n-butylphosphonium chloride, trioctylethylphosphonium bromide and tetraphenylphosphonium bromide; and crown ethers, such as 18-crown-6, dibenzo-18-crown-6 and dicyclohexyl-18-crown-6. From the economic viewpoint, quaternary ammonium salts, such as tetra-n-butylammonium bromide and tetra-n-butylammonium chloride, are preferably used.

In the case where a phase-transfer catalyst is used, the amount of the phase-transfer catalyst used is normally 0.005 to 0.5 times, preferably 0.01 to 0.2 times the weight of 2-halobenzonitrile. When the amount of a phase-transfer catalyst used is less than 0.005 times the weight of 2-halobenzonitrile, adequate catalytic effect cannot be obtained. Even when the amount of a phase-transfer catalyst used exceeds 0.5 times the weight of 2-halobenzonitrile used, additional expected effect cannot be obtained, and, therefore, it is economically disadvantageous.

In this method, a reaction solvent is not always necessary. However, in order to facilitate the reaction and the separation of the product from the reaction mixture, the use of mixed solvent composed of 0.5 to 10 parts by weight of a water-insoluble organic solvent based on 1 part by weight of water is preferred in the present invention. In many cases, better results can be obtained by the use of the mixed solvent. Water-insoluble organic solvents are not particularly limited and include hydrocarbons, such as n-hexane, n-heptane, cyclohexane, methylcyclohexane, benzene, toluene and xylene; and halogenated hydrocarbons, such as methylene chloride, 1,2-dichloroethane and chlorobenzene. The amount of the solvent used is normally 1 to 30 times the weight of 2-halobenzonitrile.

The reaction temperature for the above reaction is normally in the range of from 0° to 150° C., preferably 20° to 120° C. Reaction temperatures higher than 150° C. cause side reactions. On the other hand, the reaction rate unfavorably lowers to an impractical level when the reaction temperature is less than 0° C. The reaction time varies with the reaction temperature and the types of phase-transfer catalyst and reaction solvent and cannot be generalized, but it is normally in the range between 1 and 40 hours.

After completion of the reaction, a 2-(alkylthio) benzonitrile can be isolated and purified from the separated organic solvent layer by an ordinary procedure, such as crystallization. Since the water layer separated contains a phase-transfer catalyst, it can repeatedly be used in subsequent reactions. Therefore, almost no aqueous waste is discharged out of the solvent system. The separated organic solvent layer containing an 2-(alkylthio)benzonitrile can also directly be used for the reaction to yield a 1,2-benzisothiazol-3-one.

Next, the process in which 1,2-benzisothiazol-3-ones are obtained from 2-(alkylthio)benzonitriles will be described. Examples of halogenating agents usable in the process include chlorine, bromine, sulfuryl chloride and sulfuryl bromide, with a preference given to sulfuryl chloride and chlorine in view of reaction selectivity.

The halogenating agent is used normally in an amount of 0.8 to 3.0 moles, preferably 1.0 to 2.0 moles, per mole of 2-(alkylthio)benzonitrile. When the amount of the halogenating agent is less than 0.8 moles of 2-(alkylthio) benzonitrile, the amount of unchanged 2-(alkylthio) benzonitrile tends to increase. On the other hand, the amount of halogen used exceeds 3.0 moles, side reactions occur and lower the yield.

The water is added in the process to yield a 1,2-benzisothiazol-3-one normally in an amount of 0.8 to 5.0 moles, preferably 1.0 to 3.0 moles, per mole of 2-(alkylthio) benzonitrile. When the amount of water is less than 0.8 moles or more than 5.0 moles, side reactions occur to lower the yield.

Solvents used in the process to yield a 1,2-benzisothiazol-3-one are not particularly limited as long as they are inert to the reaction. Examples of solvents usable in the reaction include hydrocarbons, such as n-hexane, n-heptane, cyclohexane, methylcyclohexane, benzene, toluene and xylene; and halogenated hydrocarbons, such as methylene chloride, 1,2-dichloroethane and chlorobenzene. When the same solvent as used in the reaction of 2-halobenzonitrile with an alkanethiol to yield a 2-(alkylthio)benzonitrile is used in the process, a series of reactions, i.e., the reaction to obtain a 2-(alkylthio)benzonitrile and the reaction to obtain a 1,2-benzisothiazol-3-one from the 2-(alkylthio) benzonitrile, can be carried out in a one-pot process. Therefore, the production efficiency can markedly be increased. The amount of the solvent used is normally 1 to 30 times the weight of 2-(alkylthio)benzonitrile.

The reaction temperature for the process is normally in the range of from −20° to 170° C., preferably 0° to 150° C.

Reaction temperature higher than 170° C. causes side reactions. On the other hand, the reaction rate unfavorably lowers to an impractical level when the reaction temperature is less than −20° C. The reaction time varies with the reaction temperature and reaction solvent, and it is normally in the range between 1 and 40 hours.

The isolation of 1,2-benzisothiazol-3-one from the reaction mixture obtained by the above method can normally be carried out by conventional crystallization technique or by recrystallization after extraction, but other technique may be used.

Examples of 1,2-benzisothiazol-3-ones represented by the general formula (III) obtained by the method in Embodiment I or II of the present invention include:
1,2-benzisothiazol-3-one,
7-methyl-1,2-benzisothiazol-3-one,
5-butyl-1,2-benzisothiazol-3-one,
6-methoxy-1,2-benzisothiazol-3-one,
7-nitro-1,2-benzisothiazol-3-one,
6-chloro-1,2-benzisothiazol-3-one,
6-carboxy-1,2-benzisothiazol-3-one, and
6-methoxycarbonyl-1,2-benzisothiazol-3-one.

EXAMPLES

The present invention will be further described by means of the following working examples, without intending to restrict the scope of the present invention thereto.

Incidentally, the obtained product is confirmed by nuclear magnetic resonance method ($^1$H-NMR) or mass spectroscopy in order to determine whether a desired product is obtained.

Example 1

Synthesis of 1,2-benzisothiazol-3-one from 2-(methylthio)benzaldehyde in a One-Pot Process To a 500 ml four-necked flask equipped with a stirrer, a thermometer, and a condenser, 38.0 g (0.25 mol) of 2-(methylthio)benzaldehyde, 150 g of monochlorobenzene, and 91.7 g (0.275 mol) of 24.6% aqueous solution of hydroxylamine-1/2 sulfate were placed. To the above mixture in the flask, 51.2 g (0.145 mol) of 30% aqueous solution of sodium carbonate was added dropwise while stirring at a temperature of from 20° to 25° C. and allowed to react for 2 hours at the same temperature. After the completion of the reaction, the reaction mixture was heated to a temperature of from 40° to 50° C. to separate to monochlorobenzene layer and water layer. The lower water layer was discarded. The monochlorobenzene layer contained 40.9 g of 2-(methylthio)benzaldehyde oxime. The yield was 98% against 2-(methylthio)benzaldehyde.

Into the monochlorobenzene layer, 22.6 g (0.32 mol) of chlorine was introduced with stirring at a temperature of from 10° to 20° C. and allowed to react at a temperature of from 90° to 100° C. for 1 hour. After the completion of the reaction, the reaction mixture was cooled to room temperature to precipitate white crystals. The white crystals were washed with monochlorobenzene, and dried to give 34.0 g of 1,2-benzisothiazol-3-one (melting point: 157° to 158° C.). The yield of the product was 92% against 2-(methylthio)benzaldehyde oxime, and 90% against 2-(methylthio)benzaldehyde.

Example 2

Synthesis of 1,2-benzisothiazol-3-one from 2-(methylthio)benzaldehyde Oxime

The monochlorobenzene layer obtained by the same procedures as in Example 1 was condensed to precipitate crystals. The crystals were filtered and dried to isolate a 2-(methylthio)benzaldehyde oxime (melting point: 88° to 89° C.). 39.7 g of the oxime isolated was dissolved in 200 g of toluene. Then, chlorine was introduced into the mixture to react with the oxime to yield 32.7 g of 1,2-benzisothiazol-3-one. The yield against 2-(methylthio)benzaldehyde oxime was 91%.

Example 3

Synthesis of 1,2-benzisothiazol-3-one from 2-(methylthio)benzaldehyde Oxime

From the monochlorobenzene layer obtained by the same procedures as in Example 1, 2-(methylthio)benzaldehyde oxime was isolated in the same manner as in Example 2. 39.7 g of the oxime isolated was dissolved in 150 g of monochlorobenzene. Then, the oxime was cyclized in the same manner as in Example 1 except that chlorine was changed to 35.3 g (0.26 mol) of sulfuryl chloride. As a result, 32.7 g of 1,2-benzisothiazol-3-one was obtained. The yield against 2-(methylthio)benzaldehyde oxime was 91%.

Example 4

Synthesis of 1,2-benzisothiazol-3-one from 2-(methylthio)benzaldehyde Oxime

From the monochlorobenzene layer obtained by the same procedures as in Example 1, 2-(methylthio)benzaldehyde oxime was isolated in the same manner as in Example 2. 39.7 g of the oxime isolated was dissolved in 150 g of monochlorobenzene. Then, the oxime was cyclized in the same manner as in Example 1 except that blowing of chlorine was changed to dropping of 49.3 g (0.31 mol) of bromine. As a result, 32.3 g of 1,2-benzisothiazol-3-one was obtained. The yield against 2-(methylthio)benzaldehyde oxime was 90%.

Example 5

Synthesis of 1,2-benzisothiazol-3-one from 2-(methylthio)benzaldehyde in One-Pot Process To a 500 ml four-necked flask equipped with a stirrer, a thermometer, and a condenser, 38.0 g (0.25 mol) of 2-(methylthio)benzaldehyde, 200 g of toluene, and 91.7 g (0.275 mol) of 24.6% aqueous solution of hydroxylamine-1/2 sulfate were placed. To the above mixture in the flask, 51.2 g (0.145 mol) of 30% aqueous solution of sodium carbonate was added dropwise while stirring at a temperature of from 20° to 25° C. and allowed to react for 2 hours at the same temperature. After the completion of the reaction, the reaction mixture was heated to a temperature of from 40° to 50° C. to separate to toluene layer and water layer. The lower water layer was discarded. The upper toluene layer contained 40.9 g of 2-(methylthio) benzaldehyde oxime. The yield was 98% against 2-(methylthio)benzaldehyde.

To the toluene layer, 36.4 g (0.27 mol) of sulfuryl chloride was added dropwise with stirring at a temperature of from 10° to 20° C., and allowed to react at a temperature of from 90° to 100° C. for 1 hour. After the completion of the reaction, the reaction mixture was cooled to room temperature to precipitate white crystals. The white crystals were washed with toluene, and dried to give 33.7 g of 1,2-benzisothiazol-3-one (melting point: 157 to 158° C.). The yield of the product was 91% against 2-(methylthio) benzaldehyde oxime, and 89% against 2-(methylthio) benzaldehyde.

Example 6

Synthesis of 6-chloro-1,2-benzisothiazol-3-one from 4-chloro-2-(methylthio)benzaldehyde in One-Pot Process An oxime formation reaction was carried out in the same manner as in Example 1 except that 46.6 g (0.25 mol) of 4-chloro-2-(methylthio)benzaldehyde was used in place of 2-(methylthio)benzaldehyde. The upper monochlorobenzene layer contained 49.4 g of 4-chloro-2-(methylthio) benzaldehyde oxime. The yield was 98% against 4-chloro-2-(methylthio)benzaldehyde.

Into the monochlorobenzene layer, 22.6 g (0.32 mol) of chlorine was introduced with stirring at a temperature of from 5° to 15° C., and allowed to react at a temperature of from 90° to 100° C. for 1 hour. After the completion of the reaction, the reaction mixture was cooled to room temperature to precipitate white crystals. The white crystals were washed with monochlorobenzene, and dried to give 40.9 g of 6-chloro-1,2-benzisothiazol-3-one (melting point: 271° to 272° C.). The yield of the product was 90% against 4-chloro-2-(methylthio)benzaldehyde oxime, and 88% against 4-chloro-2-(methylthio)benzaldehyde.

Example 7

Synthesis of 2-(methylthio)benzonitrile

To a 500 ml four-necked flask equipped with a stirrer, a thermometer, and a condenser, 27.5 g (0.2 mol) of 2-chlorobenzonitrile, 100 g of monochlorobenzene, and 5.5 g of 50% by weight aqueous solution of tetra-n-butylammonium bromide were placed under nitrogen atmosphere.

Separately, 9.6 g (0.24 mol) of sodium hydroxide and 35.0 g of water were placed in a vessel under nitrogen atmosphere, to which 11.5 g (0.24 mol) of methanethiol was added at room temperature for 1 hour. 56.1 g (0.24 mol) of the resulting 30% by weight aqueous solution of sodium methylmercaptide was added to the above four-necked flask with stirring and refluxed for 2 hours. After the completion of the reaction, the reaction mixture was cooled to room temperature. After the solvent was distilled off, the reaction mixture was evaporated to dryness under a reduced pressure to give 29.2 g of 2-(methylthio)benzonitrile (boiling point:139° to 140° C./7 mmHg). The yield against 2-chlorobenzonitrile was 98%.

Example 8

Synthesis of 1,2-benzisothiazol-3-one

To a 500 ml four-necked flask equipped with a stirrer, a thermometer, and a condenser, 29.8 g (0.2 mol) of 2-(methylthio)benzonitrile, 100 g of monochlorobenzene, and 4.32 g (0.24 mol) of water were added. To the flask, 29.7 g (0.22 mol) of sulfuryl chloride was added with stirring at a temperature of from 5° to 15° C., heated to a temperature of from 70° to 80° C., and allowed to react for 1 hour. After the completion of the reaction, the reaction mixture was cooled to room temperature to precipitate white crystals. The white crystals were washed with monochlorobenzene, and dried to give 29.0 g of 1,2-benzisothiazol-3-one (melting point: 157° to 158° C.). The yield of the product was 96% against the starting 2-(methylthio)benzonitrile.

Example 9

Synthesis of 1,2-benzisothiazol-3-one (One-Pot Process)

To a 500 ml four-necked flask equipped with a stirrer, a thermometer, and a condenser, 27.5 g (0.2 mol) of 2-chlorobenzonitrile, 100 g of monochlorobenzene, and 2.25 g of 50% by weight aqueous solution of tetra-n-butylammonium bromide were placed under nitrogen atmosphere.

Separately, 9.6 g (0.24 mol) of sodium hydroxide and 35.0 g of water were placed in a vessel under nitrogen atmosphere, to which 11.5 g (0.24 mol) of methanethiol was added at room temperature for 1 hour. 56.1 g (0.24 mol) of the resulting 30% by weight aqueous solution of sodium methylmercaptide was added to the above four-necked flask with stirring and refluxed for 2 hours. After the completion of the reaction, the reaction mixture was separated to water (lower) layer and oil (upper) layer at 40° to 50° C. To the oil layer, 100 g of monochlorobenzene, and 3.6 g (0.2 mol) of water were added. To the flask, 27.0 g (0.2 mol) of sulfuryl chloride was added with stirring at a temperature of from 5° to 15° C., heated to a temperature of from 70° to 80° C., and allowed to react for 1 hour. After the completion of the reaction, the reaction mixture was cooled to room temperature to precipitate white crystals. The white crystals were washed with monochlorobenzene, and dried to give 29.3 g of 1,2-benzisothiazol-3-one (melting point: 157° to 158° C.). The yield of the product was 97% against the starting 2-chlorobenzonitrile.

Example 10

Synthesis of 1,2-benzisothiazol-3-one (One-Pot Process)

25.7 g of 1,2-benzisothiazol-3-one was obtained by the same procedures as in Example 9 except that 14.2 g (0.2 mol) of chlorine was introduced into the reaction mixture instead of adding sulfuryl chloride. The yield of the product was 85% against the starting 2-chlorobenzonitrile.

Examples 11 to 16

Syntheses of 1,2-benzisothiazol-3-ones 1,2-benzisothiazol-3-ones were obtained in the same manner as in Example 8 except that 2-(alkylthio) benzonitriles listed in Table 1 were used as starting materials.

TABLE 1

| Examples | 2-(alkylthio)benzonitriles | 1,2-benzisothiazol-3-ones | Yield* (%) |
|---|---|---|---|
| 11 | 3-methyl-2-(ethyl-thio)benzonitrile | 7-methyl-1,2-benziso-thiazol-3-one | 92 |
| 12 | 5-butyl-2-(methyl-thio)benzonitrile | 5-butyl-1,2-benziso-thiazol-3-one | 93 |
| 13 | 4-methoxy-2-(methyl-thio)benzonitrile | 6-methoxy-1,2-benziso-thiazol-3-one | 90 |
| 14 | 2-(tert-butylthio)-3-nitrobenzonitrile | 7-nitro-1,2-benziso-thiazol-3-one | 94 |
| 15 | 4-chloro-2-(methyl-thio)benzonitrile | 6-chloro-1,2-benziso-thiazol-3-one | 92 |
| 16 | 4-methoxycarbonyl-2-(methylthio)benzonitrile | 6-methoxycarbonyl-1,2-benzisothiazol-3-one | 90 |

*Yield of 1,2-benzisothiazol-3-ones against 2-(alkylthio)benzonitriles.

The present invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for producing a 1,2-benzisothiazol-3-one represented by formula (III), comprising reacting a 2-(alkylthio)benzaldehyde oxime represented by the following formula (II):

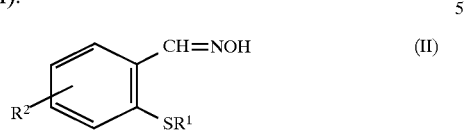 (II)

wherein $R^1$ represents an alkyl group having 1 to 4 carbon atoms, and $R^2$ represents a hydrogen atom, an alkyl group having 1 to 4 carbon atoms, an alkoxy group having 1 to 4 carbon atoms, a nitro group, a carboxyl group an ester wherein said ester is methoxycarbonyl, ethoxycarbonyl, propoxycarbonyl, or butoxycarbonyl, or a halogen atom, with a halogenating agent selected from the group consisting of chlorine, bromine, sulfuryl chloride and sulfuryl bromide to give a 1,2-benzisothiazol-3-one represented by the following formula (III):

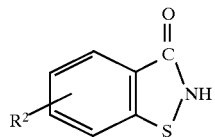 (III)

wherein $R^2$ is defined as above.

2. The method according to claim 1, wherein said halogenating agent is chlorine or bromine.

3. The method according to claim 1, wherein said halogenating agent is sulfuryl chloride.

4. The method according to claim 1, wherein the compound represented by the formula (II) is 2-(methylthio)benzaldehyde oxime.

* * * * *